(12) United States Patent
Nelson et al.

(10) Patent No.: US 7,943,158 B2
(45) Date of Patent: May 17, 2011

(54) ABSORBENT SYSTEMS PROVIDING ANTIMICROBIAL ACTIVITY

(75) Inventors: Anthony R. Nelson, Woodbury, MN (US); Susan T. Oeltjen, Lake Elmo, MN (US); Christopher J. Rueb, St. Paul, MN (US); William A. Hendrickson, Stillwater, MN (US); Kenneth R. Code, Edmonton (CA)

(73) Assignee: Biolargo Life Technologies, Inc, Irvine, CA (US)

( * ) Notice: Subject to any disclaimer, the term of this patent is extended or adjusted under 35 U.S.C. 154(b) by 709 days.

(21) Appl. No.: 12/001,073

(22) Filed: Dec. 7, 2007

(65) Prior Publication Data

US 2008/0145391 A1 Jun. 19, 2008

Related U.S. Application Data

(63) Continuation-in-part of application No. 11/516,958, filed on Sep. 7, 2006, now abandoned, and a continuation-in-part of application No. 11/516,960, filed on Sep. 7, 2006, now Pat. No. 7,867,510.

(60) Provisional application No. 60/873,763, filed on Dec. 8, 2006.

(51) Int. Cl.
*A61K 9/14* (2006.01)
*A61K 9/70* (2006.01)

(52) U.S. Cl. ........ 424/404; 424/406; 424/409; 424/443; 424/667; 424/670; 422/37; 523/122

(58) Field of Classification Search ............ 422/37; 424/404, 406, 409, 443, 667, 670; 523/122
See application file for complete search history.

(56) References Cited

U.S. PATENT DOCUMENTS

| | | | |
|---|---|---|---|
| 4,131,645 A | 12/1978 | Keblys et al. | 423/501 |
| 4,375,535 A | 3/1983 | Kightlinger et al. | 527/313 |
| 4,497,930 A | 2/1985 | Yamasaki et al. | 524/556 |
| 4,731,391 A | 3/1988 | Garvey | 521/137 |
| 4,738,847 A | 4/1988 | Rothe et al. | 424/443 |
| 4,764,418 A | 8/1988 | Kuenn et al. | 442/118 |
| 4,824,689 A | 4/1989 | Kuenn et al. | 427/2.31 |
| 4,828,912 A | 5/1989 | Hossain et al. | 442/123 |
| 4,888,118 A | 12/1989 | Barnes et al. | 210/668 |
| 4,897,304 A | 1/1990 | Hossain et al. | 442/123 |
| 4,990,338 A | 2/1991 | Blank et al. | 525/279 |
| 5,019,495 A | 5/1991 | Shanbrom | 435/1.1 |
| 5,035,892 A | 7/1991 | Blank et al. | 424/443 |
| 5,061,487 A | 10/1991 | Blank et al. | 424/78.07 |
| 5,128,149 A | 7/1992 | Shanbrom | 424/529 |
| 5,128,150 A | 7/1992 | Shanbrom | 424/533 |
| 5,176,836 A | 1/1993 | Sauer et al. | 210/670 |
| 5,186,945 A | 2/1993 | Shanbrom | 424/529 |
| 5,227,161 A | 7/1993 | Kessler | 424/94.4 |
| 5,324,438 A | 6/1994 | McPhee et al. | 210/748 |
| 5,356,611 A | 10/1994 | Herkelmann et al. | 423/501 |
| 5,360,605 A | 11/1994 | Shanbrom | 424/78.08 |
| 5,370,869 A | 12/1994 | Shanbrom | 424/78.22 |
| 5,419,902 A | 5/1995 | Kessler | 424/94.4 |
| 5,464,603 A | 11/1995 | Marchin et al. | 423/501 |
| 5,589,072 A | 12/1996 | Shanbrom | 210/638 |
| 5,609,864 A | 3/1997 | Shanbrom | 424/78.08 |
| 5,629,024 A | 5/1997 | Kessler et al. | 424/667 |
| 5,635,063 A | 6/1997 | Rajan et al. | 210/266 |
| 5,639,452 A | 6/1997 | Messier | 424/78.1 |
| 5,639,481 A | 6/1997 | Kessler et al. | 424/667 |
| 5,648,075 A | 7/1997 | Kessler et al. | 424/94.4 |
| 5,720,966 A | 2/1998 | Ostendorf | 424/402 |
| 5,772,971 A | 6/1998 | Murphy et al. | 422/292 |
| 5,800,372 A | 9/1998 | Bell et al. | 602/48 |
| 5,830,487 A | 11/1998 | Klofta et al. | 424/402 |
| 5,849,291 A | 12/1998 | Kessler | 424/94.4 |
| 5,885,592 A | 3/1999 | Duan et al. | 424/400 |
| 5,919,374 A | 7/1999 | Harvey et al. | 210/753 |
| 5,962,029 A | 10/1999 | Duan et al. | 424/613 |
| 5,962,082 A | 10/1999 | Hendrickson et al. | 427/547 |
| 6,004,465 A | 12/1999 | Uhr et al. | 210/651 |
| 6,037,019 A | 3/2000 | Kooyer et al. | 427/598 |
| 6,071,415 A | 6/2000 | Frommer et al. | 210/669 |
| 6,139,731 A | 10/2000 | Harvey et al. | 210/175 |
| 6,146,725 A * | 11/2000 | Code | 428/35.2 |
| 6,248,335 B1 | 6/2001 | Duan et al. | 424/400 |
| 6,261,577 B1 | 7/2001 | Kessler | 424/401 |
| 6,342,653 B1 | 1/2002 | Gancet et al. | 604/359 |
| 6,403,674 B1 | 6/2002 | Schubert | 522/167 |
| 6,432,426 B2 | 8/2002 | Kessler | 424/401 |
| 6,863,905 B1 | 3/2005 | Shanbrom | 424/667 |
| 7,033,509 B2 | 4/2006 | Klein et al. | 210/753 |
| 7,132,379 B2 | 11/2006 | Shanklin | 442/123 |

FOREIGN PATENT DOCUMENTS

WO    WO 02/058748 A1 *   8/2002

OTHER PUBLICATIONS

P. Kapur and M. Verma, "Determination of Iodate Ion in Presence of Cupric Ion", Industrial and Engineering Chemistry Analytical Ed.; vol. 13, No. 5 (May 1941). p. 338.

* cited by examiner

*Primary Examiner* — Sean E Conley
(74) *Attorney, Agent, or Firm* — Mark A. Litman & Associates, P.A.

(57) ABSTRACT

An article and process provides a stable technology that reduces the microbial content by providing molecular iodine to the stabilized reagents when at least two reactants are activated by aqueous and/or alcohol materials.

21 Claims, No Drawings

ABSORBENT SYSTEMS PROVIDING ANTIMICROBIAL ACTIVITY

RELATED APPLICATIONS DATA

This application claims priority from U.S. Provisional Application Ser. No. 60/873,763, filed Dec. 8, 2006 and U.S. Provisional Patent Application 60/850,976 filed Oct. 11, 2006; and continuation-in-part status under 35 USC 120 from each of U.S. patent application Ser. No. 11/516,958 filed Sep. 7, 2006, now abandoned; and U.S. patent application Ser. No. 11/516,960 filed Sep. 7, 2006, U.S. Pat. No. 7,867,510.

BACKGROUND OF THE INVENTION

1. Field of the Invention

The present technology relates to the field of antimicrobial protection, particularly antimicrobial activity in close proximity to environments that need to be protected from or cleansed of microbial or chemical material. These include closed and open environments and absorbent sheet materials that exhibit stability until activated by aqueous environments.

2. Background of the Art

It has become recognized as important to provide antimicrobial activity to surfaces that remain in contact with the bodies of patients.

Antimicrobial articles treated with virucides and germicides are known in the art. U.S. Pat. Nos. 4,828,912 and 4,897,304, both issued to Hossain et al., pertain to the use of a carboxylic acid/surfactant virucidal composition in absorbent products. U.S. Pat. Nos. 4,764,418 and 4,824,689, both issued to Kuenn et al., pertain to the addition of water-soluble humectants to carboxylic acid/surfactant virucides for use in tissue products to reduce irritation potential. U.S. Pat. No. 4,738,847 issued to Rothe et al., pertains to adding a carboxylic acid/surfactant virucide to the center ply of a three ply tissue to prevent transfer of the virucidal composition to the user, and thereby reduce irritation potential.

Irritation caused by virucidal or germicidal treatments to absorbent articles is a persistent problem. There have been attempts to ameliorate this problem by mixing the virucidal or germicidal treatment with lotions or emollients. U.S. Pat. No. 5,720,966 issued to Ostendorf, pertains to a "medicated" lotion absorbent article. The "medication" may be a virucide or disinfectant. U.S. Pat. No. 5,830,487 issued to Klofta et al. pertains to a tissue with a virucidal lotion. The lotion comprises a carboxylic acid/nonionic surfactant virucidal composition. In both the Ostendorf and Klofta, et al. patents, the intent is for the lotion to reside predominantly on the surface of the absorbent article and transfer to the user.

U.S. Pat. No. 7,132,379 describes a non-irritating multiply absorbent article made by treating an inner surface with one or more antimicrobial agents and treating the one or more outer surfaces with one or more siloxane compositions, and methods of making and using the same. The antimicrobial agent will remain confined to the inner portion of the absorbent article, thereby preventing irritation to the user, and the siloxane treated ply(s) will provide a pleasing, soothing, non-irritating tactile quality. In one embodiment, the siloxane composition comprises an amine-modified polysiloxane, in which case the product will also entrap any absorbed fluid, holding it in contact with the antimicrobial agent, and preventing it from wetting through the product and contacting the user.

U.S. Pat. No. 5,800,372 describes a field dressing for control of exsanguination. Such dressing describes the use of microfibrillar collagen and a superabsorbent polymer in a hemostatic bandage, which both absorbs blood and induces clotting.

U.S. Pat. No. 7,033,509 (Klein) discloses an iodine fluid purification process using a source of fluid; means for delivery of iodine to the source of fluid for use in the purification process. The process provides a means for recovery of the iodine and/or iodine and/or other iodine species derived from the iodine, from the fluid.

U.S. Pat. No. 5,176,836 discloses a new and improved water purification process or method by introduction of molecular iodine into the water supply to impart a desired iodine residual wherein the water is passed through an iodinated anion exchange bed wherein the concentration of $I.sub.2$ in the flowing water gradually decreases and the ion bed is recharged by treatment with an aqueous iodine solution produced by flowing water through a bed of iodine crystals having connections in parallel with the ion exchange bed and activated periodically e.g. by a timer, by measured flow of water or by residual level to recharge the bed. That system provides for long term microbiological control in water suitable for potable activities. The bed of Iodine crystals is provided with connections for flowing water there through to produce a concentrated (substantially saturated) aqueous iodine solution which is passed through the iodinated resin bed to recharge the bed with bound iodine.

The majority of patents relates to the direct or indirect treatment of water to remove microbes. Such disclosures are shown in U.S. Pat. No. 6,863,905; the use of free elemental iodine to kill or inactivate a large range of microbes (bacteria, virus and other pathogens) particularly in protein-containing solutions such as human blood, human plasma or fractions thereof is described in U.S. Pat. Nos. 5,019,495; 5,128,149; 5,128,150; 5,186,945; 5,360,605; 5,370,869; 5,589,072; and 5,609,864; pentavalent iodine-impregnated resins U.S. Pat. No. 5,635,063; provision of potable water U.S. Pat. Nos. 6,139,731 and 6,071,415; 5,324,438 describes a process for oxidizing a compound comprises contacting the compound with iodide ions and irradiating the iodide ions with UV light of a wavelength sufficient to generate iodine atoms. The compound is then oxidized with the resulting iodine atoms. The iodine atoms are reduced to iodide ions as a result of the oxidation of the compound.

The growth of many microbes is assisted by or enabled by the presence of water with the microbes. Water and aqueous materials are present in events and activities of most mammalian life forms. Aqueous solutions and dispersion and emulsions are present in blood, exudates, tears, perspiration, menstrual emissions and waste emissions of mammals. These are natural events in life cycles, but may be accompanied by contact with or attack by microbes that can have significant physical effects on the animals (including humans) and their surrounding. At a minimum, growth of some microbes in aqueous materials around the animals can develop odors, disease-carrying media, infections and death or damage to the bodies of the animals.

There are many instances where aqueous materials are retained in contact with animal bodies and in which there is potential for unwanted and even dangerous and significant microbial growth or microbial introduction into the animal body. For example, in the application of materials wound dressing, menstrual products, patches, diapers, pads and the like, moisture from the animal body or ambient conditions or the materials themselves can introduce microbes to the environment and those microbes can proliferate in the vicinity of the materials when moisture is present. The uncontrolled growth of random microbes is seldom beneficial and has been the subject of significant efforts at control.

Many applications exist where it is necessary or at the very least an advantage for agents to be present which demonstrate anti-bacterial, anti-mycotic activity or both, resulting in the control of bacterial and/or fungal growth. For example, an apparatus or article as a whole or in part may have the property of suppressing bacterial and fungal growth. Control of bacterial and/or fungal growth may be through the prevention or inhibition of the growth of such microbes.

SUMMARY OF THE INVENTION

There have been many attempts to use absorbent materials (both absorbent fibers and absorbent mass) in the protection of environments, particularly around animal bodies where waste materials carrying potentially biohazardous materials, bacteria, virus, fungus, rickettsiae, parasites and other microbial materials may be released, particularly in aqueous media such as urine, blood, weepage and the like. However, the absorbent materials become breeding grounds for microbial material and rather than protecting such environments. The antimicrobial agent serves to kill or inactivate any microorganisms, such as viruses, bacteria, or fungi that are absorbed into the tissue with body secretions or fluids, thereby inhibiting the spread of disease, such as a viral infection. Direct inclusion of strong antimicrobial materials have proved marginally effect, especially when there is any significant storage time where the microbial material may dissipate in strength, and when the strength of the antimicrobial agent is increased, the potential for irritation increases.

Absorbent systems and absorbent materials are provided to environments and patients to be treated which generate an iodine gas-rich or iodine-dissolved-in-water rich environments that can provide antimicrobial activity or antichemical activity in a controlled environment or location. The iodine environment can be provided in numerous and varied tasks and services by reactive ingredients that generate iodine. At least some of the iodine-generating components must be protected from activation by humidity or ambient moisture.

An article for application, association with or attachment to an environment that is to be treated with an iodine-rich environment upon introduction of aqueous material to the environment including the bodies of animals (including humans) to provide both absorbency and antimicrobial activity. The article and treatments may be any delivery system that can deliver the iodine-rich environment in a stable condition that can be activated as needed at an appropriate target. The delivery may be as protected reaction-ingredients and the like that may be carried in absorbent supports such as fibrous supports, film supports or otherwise deliverable forms such as diaper, gauze, padding, sanitary sheets or the like and may provided with the two reactive ingredients separated by a water-removable barrier that may comprise a water soluble, or water dispersible material; and the two reactive materials that form a composition that reacts with water to produce molecular iodine. The composition is preferably delivered to provide a local concentration of at least 10 parts per million iodine in water carried by the material when the material has 5% by weight of water present in the water absorbent with respect to the total weight of the water absorbent material or concentrations that are sufficiently concentrated in air to address antimicrobial requirements or provide sufficient chemical activity to mediate the concentration of the targeted chemical in the environment.

DETAILED DESCRIPTION OF THE INVENTION

The present technology relates to the provision of articles, such as sheets, films, masses or the like to an environment around a patient (animals including humans) where liquid that might contain biohazardous material, and especially microbial material might be released, needs to be absorbed to prevent environmental contamination, and yet must remain in place for various periods of time (minutes, hours and even days) without allowing microbial growth to be uncontrolled in the device and the environment. The present technology uses iodine generating reactants within an absorbent mass to provide the antimicrobial activity, and stabilizes the reactants so that ambient humidity will not cause the reactants to prematurely release the iodine and thereby reduce the effectiveness of the device when release is needed and avoid unsightly discoloration of the environment because of iodine staining. Articles, methods of stabilization, methods of manufacture and devise are disclosed herein.

One basic technology described herein comprises a process for the stabilization of two reactants that form iodine in the presence of water. The at least two reactants (reagents) are stabilized by providing at least two solid reactants in particulate form that when dissolved or dispersed together in water generate iodine. A coating (layer, film, continuous, discontinuous, multilayered etc.) is provided on at least one of the at least two reactants in particulate form with a layer that is disruptable, dispersible or soluble in an aqueous material or alcohol (e.g., water, aqueous solution, dispersion or suspension, alcohol or alcohol solution, suspension or dispersion) to form at least one coated reactant. The at least one coated reactant is then combined with another of the at least two solid reactants into a single milieu including the coated reactant. The term "milieu" is a generic term encompassing any format, as later exemplified in detail, which can carry, transport or support the at least two reagents with the coated reagent in a deliverable form. The coating may comprise a stand-off coating of stand-off particles having a diameter that is less than 20% of average particle diameters for the at least one of the at least two reactants. Stand-off particles are solid or gel particles that are supported on the surface of the reactant particles to form a physical separation between the coated particle and uncoated particle to prevent intimate contact between adjacent particles, even when contacted by co-confinement in a single container. The stand-off particles, as further described herein, may allow penetration of humidity to the coated reactant, but the physical separation between the reactants established by the stand-off particles prevents the moisture or small amount of water from forming a reactive environment that brings the two reactants together (e.g., a solution or dispersion). The stand-off particles may form a discontinuous coating on surfaces of the at least one reactant particles. The stand-off particles preferably may have a diameter that is less than 20%, less than 10% and less than 5% of average particle diameters for the at least one of the at least two reactants that is coated. The stand-off particles may comprise inorganic oxide particles or organic polymeric particles, by way of non-limiting examples. The coating may alternatively comprise a coating of a water-soluble material, such as a water-soluble polymer. The coating may alternatively comprise a coating of a water-dispersible material. The at least two reactants preferably comprise XY and ZI, wherein X is a metal, Y is an anion, Z is an alkali metal or alkaline cation and I is Iodide, and most preferably comprise $Cu^{+2}SO_4^{-2}$ and $K^+I^-$. The method may be practices wherein iodine is released to an environment by contacting the milieu with sufficient aqueous material to breach the coating and allow the at least two reactants to react to generate iodine in at least the aqueous material. The method may also be practiced wherein the at least one coated particle is retained in the milieu by bonding of the water-soluble coating with solid material in the milieu.

The milieu may be preferably selected from the group consisting of a) mixtures of particles, b) mixtures of particles with a carrying medium, c) packets of particles, d) fabric containing particles, e) compacted pellets, and f) combinations of a), b), c), d) and e. Capsules, free-flowing powder mixtures, multicompartmental packets, separate compacted pellets and the like are included within these descriptions. In one preferred embodiment, the milieu comprises fabric in a structured form that retains its shape when contacted with the aqueous material. By structured form is included at least sheets, face masks, fitted covers, shaped garments, preformed size sheets or pads, and the like. The method of release further may use an aqueous material further comprising alcohol, which may accelerate iodine release or concentrate the iodine released. The at least two reagents, including the at least one coated reagent are combined with fabric material prior to establishing a final structured form of the fabric so that the fabric physically retains the at least two reagents in the structured form. For example, the particles may be mixed with fibers and/or filaments before compacting, interleaving, weaving, knitting, bonding, twining and the like. The particles may be provided with additional adhesive or binding agent to secure them within the fabric, or the coating on one or more of the reagent particles may physically secure the particles (by adhesion or bonding) to elements of the fabric.

A water retaining milieu according to one embodiment of the present technology that provides antimicrobial activity may comprise: at least one layer comprising an absorbent mass and at least two reactants that generate gaseous iodine in the presence of water; the at least one layer containing barrier material between the two reactants that is stable for at least 10 hours at 50% relative humidity at 70° C. and is penetrable by direct contact with water comprising at least 25% by weight of the at least two reactants so that the reactants generate iodine gas.

One general description of a process according to the technology disclosed here is a process for reducing the growth rate of microbial content in an article. The method provides an aqueous- or water-absorbent mass in the environment to be protected. The device will release iodine gas after the mass imbibes an aqueous material. The device, usually comprising a sheet, film, fabric or the like, as a bed sheet, diaper, wrap, bandage, gauze, compress, applique', gown or the like is provided into the environment of a live user. The article comprises at least two reactants that form gaseous iodine when immersed in water. The at least two components being with ±75% stoichiometric equivalence and the at least two and preferably two classes of reactants comprising at least 5% of the total solid weight of at least one layer within the absorbent mass in which the reactants are contained and at least 25% of the remainder of the layer comprising an aqueous-absorbing mass. The article is stable in 50% relative humidity at 70° C. for 10 hours without delivering at least 5% of the theoretic iodine available to the environment from the total of the at least two reactants in that 10 hour period, stability being provided by provision of a water disruptable barrier between the two reactants.

The term water-disruptable includes soluble, dispersible, water porosity-inducing or sufficient weakening of the coating that modest shear forces would open up the coating to penetration by direct contact by water. Coating such as water-dispersible or soluble polymers such as, but not limited to acrylates, polyvinyl alcohol, polyvinylpyrrolidone, amylase-derived polymers, silicates, metalsilicates (e.g., sodium-, potassium-, calcium-, magnesium-, aluminum-metsasilicate), gums, resins and the like. The article is preferably provided to the user as a diaper, compress, wrap, bandage, gauze, tourniquet or sheet. The at least two reactants react in the presence of water to generate a concentration of at least 10 parts per million in the water (or aqueous medium) of the molecular iodine. The humidity barrier is best provided as a coating over at least one of the at least two reactants that is dissolved, disrupted or made porous to water in the present of an aqueous material comprising at least 25% by weight of the two reactants. Porosity may be obtained with a water-insoluble film having soluble polymer or salts in the film structure. The preferred medium for the at least two reactants is when they are carried within a superabsorbent mass in the article and wherein molecular iodine gas is generated within the superabsorbent mass and some is dissolved in aqueous material retained by the superabsorbent mass. The preferred process is where the reaction to form the molecular iodine is represented by $$XY + ZI \rightarrow X° + ZY + I_2$$

wherein X is a metal, Y is an anion, Z is an alkali metal or alkaline cation and more preferably where the reaction to form the molecular iodine is represented by $$Cu^{+2}SO_4^{-2} + K^+I^- \rightarrow Cu° + K_2SO_4 + I_2.$$

A water (or aqueous material) retaining device described herein may have antimicrobial activity and a structure comprising:

at lest one layer comprising an absorbent mass and at least two reactants that generate gaseous iodine in the presence of water;

the at least one layer containing barrier material between the two reactants that is stable for at least 10 hours at 50% relative humidity at 70° C. and is penetrable by direct contact with water comprising at least 25% by weight of the at least two reactants so that the reactants generate iodine gas. The absorbent mass preferably comprises at least 25% by weight of a superabsorbent polymer wherein the reaction to form the molecular iodine is represented by $$XY + ZI \rightarrow X° + ZY + I_2$$

and X is a multivalent metal, Y is a multivalent anion, and Z is an alkali metal or alkaline cation; and XY is present as at least 1% by weight of the absorbent mass and ZI is present as at least 3% by weight of the absorbent mass. At least one of XY and ZI preferably are coated with a humidity stable and water penetrable coating. The superabsorbent polymer preferably comprises an acrylic resin (e.g., an alkali metal or alkaline metal acrylic acid salt polymer) and the concentration of XY is at least 3% by weight of the absorbent mass and the concentration of ZI is at least 7% by weight of the absorbent mass.

One way of providing molecular iodine ($I_2$) on site with a patient, rather than having to find a way of transporting it to a site) is to provide reactants that can readily produce molecular iodine on-site in a controllable reaction. One format of providing the molecular iodine would be through the oxidation-reduction reaction between two salts o4r compounds to produce the molecular iodine. It is a readily controlled environment where the reaction can be performed in an aqueous environment. One reaction that can effect this would be generically described as:

$$X^+Y^- + Z + I^- \rightarrow X° + Z^+Y^- + I_2$$

In this reaction scheme, X is a metal (preferably a multivalent metal and more particularly a divalent metal), Y is an anion (preferably a multivalent anion and more preferably a divalent anion, and an anion having at least two oxygen atoms), Z is an alkali metal or alkaline cation. Examples of X are copper, iron, manganese, lead, nickel, tin, and the like, Y can be sulfate, sulfite, sulfonate, carbonate, phosphate, phosphate, nitrate, nitrie, borate, and the like, and Z can be sodium, lithium, potassium, ammonium, magnesium, aluminum, and the like. One preferred reaction would be:

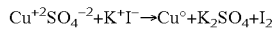
$$Cu^{+2}SO_4^{-2}+K^+I^-\rightarrow Cu^\circ+K_2SO_4+I_2$$

This reaction takes place readily in an aqueous environment and produces molecular iodine at a controlled rate. The reaction may be used by wetting, dispersing or dissolving the molecular iodide and allowing the iodine in the carrying material be released and carried to the site 9 which may be the carrying material itself, such as the fabric, clay, fibers, film etc.) penetrate the area intended to be treated. The iodine may persist for sufficient time to treat the area, particularly within a wetted material on the surface of a patient. The reaction may also be used by dispersing or mixing the two ingredients into the carrying material (e.g., the fabric, fiber, film, sheet, etc.), either with additional water provided, with water of hydration on the first reactant (e.g., $X^+Y^-.nH_2O$, such as $CuSO_4.5H_2O$) or with ambient water in the carrying material. The two reactants may be physically separated from each other before being combined for application or reaction, as in separate capsules, fibers, layers or the like. The two reactants may be provided as a solid carrier medium that separates the two reactants until they are in contact with water (as in a soluble carrier such as polyvinyl alcohol, gelatin, amylase, sugars and the like, in pellet, fiber, dust, particle or block form). The two reactants may be independently coated with a soluble/dispersible coating and the two ingredients kept in a single water-penetrable layer.

Although the materials of the described technology may be provided in a vast array of materials and compositions applied to the surface of patients, such as bandages, bandaids, diapers, gauze, wraps, sanitary napkins, tampons, plugs, sheet coverings 9 e.g., on beds) and the like, the discussion will emphasize diapers and incontinence diapers for simplifying the disclosure, without intending to limit the scope of the invention.

The composition is preferably delivered to provide a local concentration of at least 10 parts per million iodine in water carried by the material when the material has 5% by weight of water present in the water absorbent with respect to the total weight of the water absorbent material or concentrations that are sufficiently concentrated in air to address antimicrobial requirements or provide sufficient chemical activity to mediate the concentration of the targeted chemical in the environment. In terms of relative compositions in the absorbent material, the material may comprise at least 1% by weight of metal reactant and at least 4% by weight iodine reactant, preferably at least 2% or 3% metal reactant and correspondingly 5% to 7% iodine reactant and most preferably at least 5% (preferably up to 10% metal reactant and 8-18% iodine reactant. The majority of the remaining material may be the absorbent or preferably superabsorbent material or combinations of absorbent and superabsorbent materials, with any desirable adjuvants, such as color indicators that are activated upon release of iodine, anti-inflammatants, skin aids, and the like.

A test may be carried out in accordance with JIS K 7223 "Method for Water Absorption Test of Super Absorbent Polymer" to measure the liquid retention ratio. A nonwoven fabric sample 7 cm² was dipped in artificial urine (prepared by dissolving 9 g of sodium chloride, 20 g of urea and 1 g of creatine in 1 liter of deionized water) for 2 hours, thereby enabling the sample to retain artificial urea. After a lapse of 2 hours, the sample was allowed to stand while its corner was vertically suspended with a hook for 15 minutes to remove excess artificial urea which could not penetrate into a tea bag. After leaving for 15 minutes, the weight (Wc) was measured. This sample was dried and the dry weight (Wd) was measured. The liquid retention ratio was calculated by before and after weight measurements. Examples of useful superabsorbent polymers may be found, by way of non-limiting examples, in U.S. Pat. Nos. 6,342,653; 5,061,487; 5,035,892; and 4,990,338.

A general description of superabsorbing polymers includes Sodium polyacrylate, crosslinked (monomer residue in the polymer backbone: —CH2-CH(CO2Na)—), which is a crosslinked acrylic acid polymersodium salt, invented by the Dow Chemical Company. Polymers were produced which absorbed up to 10,000 times their weight in distilled water (gel capacity) and are called polyelectrolytes. These polymers are referred to as "Super Absorbents". When dry, the polymer appears as a white powder and when in gel form it is a transparent slush/gel. It is used in diapers, tampons, bed pads, fire control; spray drift control, seed germination, soil conditioning, and hydroponics. It is hard water and salt sensitive in that dissolved minerals greatly reduce the absorption capacity of the gel. Other high-gelling capacity crosslinked salts of polyacrylic acid include potassium, lithium, and ammonium salts. Sodium polyacrylate can absorb more than 300 times its weight of tap water and 800 times its weight in distilled water.

Sodium polyacrylate is a polymer containing many acrylate monomers connected end-to-end in a large chain. Crosslinks between chains "tether" the chains together (FIGURE). The more cross-links the polymer has, the higher the density of the polymer. Superabsorbent polymers are actually partially neutralized polyacrylate. This means that anywhere from 50-70% of the COOH acid groups (FIGURE) have been converted to their corresponding sodium salts.

Water is drawn into the beads—and hence the core of the diaper—by osmotic pressure. As the water is drawn in, the polymer swells and develops the gel-like consistency. The driving force for the osmotic pressure is the higher concentration of sodium ions in the beads than in the outside water. Water is drawn into the polymer in an attempt to balance the number of ions inside and outside the polymer. This is why the polymer can absorb more distilled water than tap water. Tap water already contains some ions and the osmotic pressure is lower between the bead and the outside water. Manufacturers are able treat the outside of the beads to increase the cross-link density of the shell around the bead, forming a bead with a higher crosslink density at the surface than in the interior. This denser shell enables the beads to hold water under a weight-bearing load. The tighter shell prevents leakage.

The term 'superabsorber' encompasses a number of polymers all having the basic ability to absorb massive quantities of water. Four commonly used superabsorbers include sodium polyacrylate, polyacrylamide crystals, polyacrylamide plant spikes, and Gro-Creatures. While each polymer may have a somewhat different mechanism used to achieve the superabsorbing phenomenon and the rates of absorption can differ, they all effectively absorb water. All are essentially hydrophyllic non-toxic crosslinked polymers that can absorb several hundred times (e.g., at least 200 times) their weight in water, but do not dissolve because of their three-dimensional polymeric network structure. They are fascinating materials and very versatile because of their unique solubility and transport properties. The liquid-like properties result from the fact that the polymer is composed almost entirely of water. However, the polymer also exhibits solid-like properties due to the network formed by the crosslinking reaction.

At least one of the two reactants carried in the absorbent mass must be encapsulated, coated or otherwise separated from the other ingredient. The barrier created between the two ingredients must be removable by exposure to an aqueous environment by dissolution, disruption, dispersion or sufficient softening that mild physical shearing would disrupt the barrier, allowing the water to combine the two active ingredients. It is desirable for the barrier to be stable for at least 10 hours at 50% relative humidity at 70° F., and more preferably for 10 hours at 70% relative humidity and 70° F. Barrier materials may be provided by any coating technology such as spray encapsulation of individual ingredient(s), iontopherisis deposition, chemical vapor deposition, sputter coating, particle impact deposition (as described in U.S. Pat. No. 5,962,082, which is also useful for solid to solid deposition), and any other known coating procedures.

The technology described herein is performed by applying a solid carrier system to a patient, and awaiting the presence of sufficient water on or in the carrier system to activate the ingredients and cause the gaseous iodine to form in sufficient concentration in the solid carrier to attenuate, reduce or eliminate bacterial growth in the solid carrier. A simple format, in considering diaper-like materials for any age animal, would include at least the following formats:

1) particulate and separate reactants may be carried in the same layer of the carrier (generally referred to as a diaper, but inclusive of any wrap, sheet, pad, gauze, bandage, compress or the like placed into contact with a patient);
2) particulate and separate reactants may be carried in different layers of the diaper;
3) particulate reactants may be carried in the same pellets in an anhydrous condition in the same layer of a diaper;
4) the particulate reactants may be adhered to the same or separate fibers or films that are associated with on constitute the diaper;
5) the reactants may be carried in fiber materials dispersed throughout or partially constituting the structure of the diaper;
6) capsules or microcapsules of the reactants in water-soluble or water-dispersible shells may be distributed throughout the diaper; and
7) a film or films (water-soluble, water-dispersible or water-leachable) may carry one or more of the reactants, with the other reactant in a location that released or carried first reactant will be placed into contact with the second reactant in the presence of water.

Other formats and process may be used as long as the presence of water on the carrier system enables the generation of gaseous molecular iodine within the carrier in sufficient concentration to act as a microbicide.

The process may use the above reaction to form the molecular iodine represented by $$XY+ZI \rightarrow X°+ZY+I_2$$

wherein X is a metal, Y is an anion, Z is an alkali metal or alkaline cation, or where X is a multivalent metal, Y is a multivalent anion, and Z is an alkali metal or alkaline cation, and is preferably represented by $$Cu^{+2}SO_4^{-2}+K^+I^- \rightarrow Cu°+K_2SO_4+I_2.$$

The process may be performed where the two reactants are carried in a superabsorbent polymer. The solids carriers for the two reactants may also include compositions of the present that comprise superabsorbent or non-superabsorbent polymers, natural products (e.g., papers, cellulosic solids, water-insoluble porous materials which absorb or adsorb the film-forming material within the structure, water-soluble porous materials which absorb or adsorb the film-forming material within the structure, porous containers which merely slowly release a volume of the film-forming material, porous containers which both dissolve and physically release volumes of the film-forming composition through pores, and the like. In general, selection of an effective application rate can depend on habitat depth, surface debris, emergent and surface vegetation, organic matter, microbial and algal concentration, the specific target species, and the developmental stage of the target species. Superabsorbent polymers are described, by way of non-limiting examples in U.S. Pat. Nos. 6,403,674; 4,731,391. Superabsorbent polymers, including starch graft co-polymers, are known in the art. See, for example, those described in U.S. Pat. Nos. 4,375,535 and 4,497,930 (incorporated herein by reference), which have disclosed uses as adhesives, flocculants, sizes, water-retaining materials for agriculture and water-absorbing materials for sanitary materials. However, the spectrum of advantages attendant the use of superabsorbent polymers in solid and flowable terrestrial insecticidal, pesticidal or insecticidal/pesticidal delivery compositions have gone unrecognized.

The superabsorbent polymers of the present invention are synthetic organic polymers which are solid and hydrophilic, absorbing over 100 times their weight in water. These superabsorbent polymers are typically in a powder, granule, extruded, or flake form, adapted to be blended and/or agglomerated into any shape or form.

The superabsorbent polymers may be, for example, acrylamide alkali metal acrylate co-polymers; propenenitrile homo-polymers, hydrolyzed, alkali metal salts; polymers of propenamide and propenoic acid, alkali metal salts; hydrolyzed acrylonitrile co-polymers, and starch graft co-polymers and ter-polymers thereof. All of these are designed to be hydrophilic, absorbing over 100 times their weight in water. The resulting hydrophilic polymers can absorb from over one hundred to greater than about 5000, more typically around 500 to about 1,000, times their own weight in water (measured using distilled water, pH 7.5, 25, 760 mm Hg. absorption within about 30 seconds). However, the absorption or swelling capacity and absorption or swelling time typically varies with each specific superabsorbent polymer.

One class of superabsorbent polymers include combinations of a starch and organic monomers, oligomers, polymers, co-polymers or ter-polymers. They may be manufactured in a variety of ways, for example, the methods described in U.S. Pat. Nos. 4,375,535 and 4,497,930, and can be, for example, the product of grafting corn starch (amylopectin) with acrylonitrile (an acrylic monomer or oligomer). A second class of superabsorbent polymers includes combinations of acrylamide and acrylate polymers, co-polymers and ter-polymers.

The following examples are provided as prophetic descriptions of formats for delivery of technology according to the descriptions of the present invention.

Land mass, such as soil and sand, can be contaminated by microbes in a number of manners. The most common manner of soil contamination is from improper handling or disposal of organic wastes and sewage. Excessive rainfall can also stress sewage systems, causing them to overflow and spill raw sewage over the land. Whatever the source of the microbial contamination, the danger to animal life can persist for extended periods of time and can severely affect both the medical and economic health of an area. It is therefore essential that methods and plans be developed that can treat a wide variety of microbial contaminations, and do so in a rapid manner and at acceptable costs. The problem has been that soil mediation or repair is far more complex and difficult than water purification techniques.

Water can be readily transported through pipes into treatment areas, through filters, or be loaded with chemistry that rapid spreads through the water system to attack microbes. Land mass can not be moved about as readily, and materials added to soil do not disperse as widely as materials added to aqueous systems. Materials added to soil for purposes of microbe reduction or elimination must not persist beyond their useful life and must not contribute a contamination effect themselves.

The technology disclosed herein is based on the discovery that the provision of molecular iodine into microbially contaminated land mass (e.g., soil or sand) can mediate the land mass by killing or at least reducing the concentration of the vast majority of microbes that would ordinarily persist in the land mass.

Land mass (generally soil and/or sand) may become contaminated with any variety of microbes that may be harmful to vegetation or fauna that come into contact with the microbes. The land mass is then treated with molecular iodine in vapor or dissolved liquid form to provide a concentration in water or aqueous mass of at least about 10 parts per million. The molecular iodine (as opposed to iodide anion) is provided as a) a gas, b) liquid or c) provided as two reactants that form molecular iodide (s a gas or into a liquid) in the soil, either by using an aqueous carrier, water of hydration or ambient ground water. The source of molecular iodine may be topically applied, ploughed into the soil, mixed into the soil, injected into the soil, sprayed onto the soil, or otherwise applied where desired. Elemental iodine is a biocidally active form of iodine that has been used as a water disinfectant for almost a century. It is also widely used as a sanitizing compound in the food processing industry. Chlorine solution (especially hypochlorites) have been widely using by growers as a sanitizing wash for many fruits and vegetables. However, the strong oxidizing effect of chlorine in water with a moderate to high organic load results in a number of different complex compounds (trihalomethanes or THM) which can become a significant environmental hazard. There are strong reasons to minimize the excessive use of chlorine in the environment.

One way of providing molecular iodine ($I_2$) on site, rather than having to find a way of transporting it to a site) is to provide reactants that can readily produce molecular iodine on-site in a controllable reaction. One format of providing the molecular iodine would be through the oxidation-reduction reaction between two salts to produce the molecular iodine. It is a readily controlled environment where the reaction can be performed in an aqueous environment. One reaction that can effect this would be generically described as:

$$X^+Y^- + Z + I^- \rightarrow X^\circ + Z^+Y^- + I_2$$

In this reaction scheme, X is a metal (preferably a multivalent metal and more particularly a divalent metal), Y is an anion (preferably a multivalent anion and more preferably a divalent anion, and an anion having at least two oxygen atoms), Z is an alkali metal or alkaline cation. Examples of X are copper, iron, manganese, lead, nickel, tin, and the like, Y can be sulfate, sulfite, sulfonate, carbonate, phosphate, phosphate, nitrate, nitrie, borate, and the like, and Z can be sodium, lithium, potassium, ammonium, magnesium, aluminum, and the like. One preferred reaction would be:

$$Cu^{+2}SO_4^{-2} + K^+I^- \rightarrow Cu^\circ + K_2SO_4 + I_2$$

This reaction takes place readily in an aqueous environment and produces molecular iodine at a controlled rate. The reaction may be used, as intimated above, by either causing the reaction to occur in a container and directing the iodide into the soil (as by gas injection) or by dissolving the molecular iodide and injecting or spraying the dissolved iodide into or onto the soil. The reaction may also be used by dispersing or mixing the two ingredients into the land mass, either with additional water provided, with water of hydration on the first reactant (e.g., $X^+Y^-\cdot nH_2O$, such as $CuSO_4\cdot 5H_2O$) or with ambient water in the land mass. The two reactants may be physically separated from each other before being combined for application or reaction, as in separate pouches or containers. The two reactants may be provided in a solid carrier medium that separates the two reactants until they are in contact with water (as in a soluble carrier such as polyvinyl alcohol, gelatin, amylase, sugars and the like, in pellet or block form). The two reactants may be provided as liquids in separate containers to be mixed immediately before application. The two reactants may be independently coated with a soluble/dispersible coating and the two ingredients kept in a single water-tight container.

If provided in solid form (e.g., pellets, grains, tablets, powder, blocks, etc), the solid is preferably mixed into the soil rather than merely spread on top of the soil or sand, so as to prevent winds from blowing the solid away. If the solids are sufficiently large (e.g., at least 1.0 mm, preferably at least 2.0 mm in diameter), they can be more safely sprinkled on the surface of the soil or sand without as much concern of being blown away or unevenly distributed by the wind. The solids may be otherwise ploughed into the soil or sand, raked into the soil or sand, injected into the soil or sand, mixed with solid and sand and deposited onto the soil and sand or otherwise securely applied.

It will be apparent to one skilled in the art that there are various reactant chemicals that can be used. The reaction between anhydrous cupric sulfate and potassium iodine to produce iodine is one which is known in the art. Generally two parts (molecular stoichiometry) potassium iodine is required for every one part of anhydrous cupric sulfate to produce the desired reaction. In order to avoid problems in implementing the invention with the chemicals described above, the following matters should be noted. When using container or mixing prior to application, non-ferrous mixing containers and non-ferrous application instruments (or polymer coated ferrous material) should be used in order to avoid galvanic depositing of copper from solution. Application with absorbent and superabsorbent carriers (acrylic polymers, for example) has been found to require an additional amount of cupric sulfate over and above that used for the reaction. The reason for this is believed to be that the substrate has a tendency to sequester multivalent ions. With mixing in the vicinity of workers, care should be taken to consult safety data sheets relating to iodine gas before experimentation of any magnitude is conducted.

Soil microorganisms tend to congregate at the soil surface in a shallow layer of approximately 10 centimeters in depth. This shallow layer is referenced as either the weathering layer or the plough layer. The large majority of food (leaf fall, plant and animal detritus, etc.) is available at the soil surface. Natural biodegradation end products are fulvic and humic acids which may take up to 25-30 years to biodegrade. Microbial population size bears a direct relationship to the availability of food sources. A distribution of microorganisms may exist in the initial 75 centimeters of a soil profile and may include aerobic bacteria, anaerobic bacteria, actinomycetes, fungi, viruses, rickettsiae and algae. The total aerobic and anaerobic bacteria in the upper 8 cm of soil may be 77-80 percent of the total bacteria found in the 75 cm. profile. 95 percent of all bacteria may be found in the upper 25 cm. of the soil profile. Aerobic bacteria may average between 80-90 percent of the total bacteria for the soil horizons investigated. Thus it is desirable that the gas be provided through the major portions of this depth, e.g., at least to 8-25 centimeters.

Iodine is the preferred sanitizing agent in the food industry as it is acknowledged as a more effective user friendly sanitizing agent than chlorine. In addition, depending upon the concentrations, it is safe, can be effectively used at reduced concentrations (up to ten times less) than chlorine yet with a higher microbial kill rate. Iodine (unlike chlorine) does not produce any harmful substances such as carcinogens, and if nearly all by-products are removed, can produce an environmentally safe waste water. Being a solid at room temperatures and supplied, immersed in water, the potentially harmful effects of exposure to a concentrated sanitizing agent such as chlorine are removed, significantly improving environmental work conditions. Furthermore, iodine is less corrosive than chlorine reducing corrosive effects from the use of a biocide.

A number of United States patents disclose the use of iodine in conjunction with processes for purification of water. For example, U.S. Pat. No. 4,888,118 discloses a water purification process in which the water is passed through a mass of nylon 4 complex with iodine. The treated water is subsequently passed through nylon 4 to remove iodine from the water.

One of the difficulties with the known systems is to maintain an optimum amount of active iodine delivered into the target water supply for the specified purpose. To date there has been no effective system which can effectively and economically guarantee the delivery of exactly the right amount of active iodine at higher levels into the water used to wash produce in the case where iodine is used for food sanitization or into water delivered through reticulation networks, not only to prevent waste of iodine and economic loss but also to ensure that there is an acceptable minimum of active iodine.

Iodine recovery processes are known whose objective is to recover iodine to compensate for gradual reduction of $I_2$ in the flowing water and to provide a desired iodine residual. The process described in U.S. Pat. No. 5,176,836 is distinguished from previous systems by providing a continuous long term microbiological control process in a water supply particularly in space vehicle applications wherein $I_2$ is released into the water stream flowing through a suitable anion exchange resin.

U.S. Pat. No. 5,919,374 discloses a method and apparatus for producing bacteria free iodine species containing drinking water for farm animals under continuous dynamic water flow to produce a saturated iodine species containing aqueous solution at a pre selected temperature and blending the saturated solution with a second water flow to produce a diluted iodine species bacterium free aqueous solution.

U.S. Pat. Nos. 4,131,645; 5,356,611; 5,464,603; 5,639,452; 6,139,731; and 6,004,465 disclose prior art processes in which iodine is employed, each of which is incorporated herein by reference. The processes described in those US patents do not teach the use of means to effectively and economically control delivery of iodine in a water stream, nor do they disclose collection and conversion of iodide to iodine species for re use in the process.

Iodinated resin beds are known as a means for recharging a water supply with a minimum amount of active iodine. The recharging is effected by treatment with an aqueous iodine solution produced by flowing water through a bed of iodine crystals. The iodine residual is monitored and the bed recharged where necessary by adjusting the flow rate of water through the bed of iodine crystals. This is an expensive method of monitoring the level of active iodine and the resin rich in bound iodine is very expensive. In addition, the capacity of the resin is limited and reloading techniques in the field would be difficult to maintain in high water flow conditions. Also, this process is best suited to low level (<4 ppm) delivery of active iodine usually in a clean filtered water environment. This is due to the slow dissolving rate of iodine from known iodine beds and the limitation of the release rate and saturation of the anion exchange resins.

An ideal level of active iodine to be maintained in the aqueous content in the soil or sand is in the range of at least or greater then 10 ppm to 25 ppm although some applications may require higher concentrations. When iodine is used in large spill sanitizing applications, it may react with organic matter in which case the active iodine can be reduced to the point where there is little left for microbiological control. If resins (e.g., superabsorbing polymers) are used to deliver active iodine, this could necessitate continual monitoring of iodine concentration. It is expensive to use resin in large areas of soil, so it is likely that this mode of delivery would be used in more localized areas. Saturation of resin with 46% weight iodine will produce around 4 ppm active iodine release, which is insufficient alone, but with the reactive mixture, higher concentrations of molecular iodine can be provided. A controlled iodine delivery process would be one in which the level of iodine can be maintained at a predetermined optimum level and without constant manual intervention and monitoring.

The process technology of the present disclosure may be practiced in a number of formats, such as a process for reducing the microbial content in land mass by providing molecular iodine in the land mass in a concentration in aqueous material in the land mass of at least 10 parts per million. The aqueous material should have a concentration of at least 10 parts per million is applied to the land mass. Specific formats include two reactants are added to the land mass and the two reactants react in the presence of water to generate a concentration of at least 10 parts per million in the water of the molecular iodine, especially where the two reactants are a) mixed with the land mass and at least some of the water present is ambient water; b) mixed with the land mass and at least some of the water present is water of hydration of one of the two reactants; c) mixed with the land mass and at least some of the water present is applied to the land mass at about the same time as the application of the two reactants; d) mixed with the land mass and at least one of the two reactants is coated to prevent premature reaction with water or another reactant. The process is particularly useful on recently contaminated sites, especially where the contaminant microbes reside in the top 25 cm of the soil such as where the land mass is sand at a site where organic waste matter has contaminated the san with microbes.

Among the ways of applying the molecular iodine are at least where molecular iodine gas is injected into the land mass; where the molecular iodine gas is generated in a closed container and injected into the land mass; where the land mass is physically disturbed to assist mixing of molecular iodine into the land mass; where physical disturbance comprises plowing of the land mass; and where solid reactant material to generate the molecular iodine is deposited in the land mass by the physical disturbance. The process may use the above reaction to form the molecular iodine represented by $$XY + ZI \rightarrow X^\circ + ZY + I_2$$

wherein X is a metal, Y is an anion, Z is an alkali metal or alkaline cation, or where X is a multivalent metal, Y is a multivalent anion, and Z is an alkali metal or alkaline cation, and is preferably represented by $$Cu^{+2}SO_4^{-2}+K^+I^- \rightarrow Cu^\circ + K_2SO_4 + I_2.$$

The process may be performed where the two reactants are carried in a superabsorbent polymer. The solids carriers for the two reactants may also include compositions of the present that comprise superabsorbent or non-superabsorbent polymers, natural products (e.g., papers, cellulosic solids, water-insoluble porous materials which absorb or adsorb the film-forming material within the structure, water-soluble porous materials which absorb or adsorb the film-forming material within the structure, porous containers which merely slowly release a volume of the film-forming material, porous containers which both dissolve and physically release volumes of the film-forming composition through pores, and the like. In general, selection of an effective application rate can depend on habitat depth, surface debris, emergent and surface vegetation, organic matter, microbial and algal concentration, the specific target species, and the developmental stage of the target species. Superabsorbent polymers are described, by way of non-limiting examples in U.S. Pat. Nos. 6,403,674; 4,731,391. Superabsorbent polymers, including starch graft co-polymers, are known in the art. See, for example, those described in U.S. Pat. Nos. 4,375,535 and 4,497,930 (incorporated herein by reference), which have disclosed uses as adhesives, flocculants, sizes, water-retaining materials for agriculture and water-absorbing materials for sanitary materials. However, the spectrum of advantages attendant the use of superabsorbent polymers in solid and flowable terrestrial insecticidal, pesticidal or insecticidal/pesticidal delivery compositions have gone unrecognized.

The superabsorbent polymers of the present invention are synthetic organic polymers which are solid and hydrophilic, absorbing over 100 times their weight in water. These superabsorbent polymers are typically in a powder, granule, extruded, or flake form, adapted to be blended and/or agglomerated into any shape or form.

The superabsorbent polymers may be, for example, acrylamide alkali metal acrylate co-polymers; propenenitrile homo-polymers, hydrolyzed, alkali metal salts; polymers of propenamide and propenoic acid, alkali metal salts; hydrolyzed acrylonitrile co-polymers, and starch graft co-polymers and ter-polymers thereof. All of these are designed to be hydrophilic, absorbing over 100 times their weight in water. The resulting hydrophilic polymers can absorb from over one hundred to greater than about 5000, more typically around 500 to about 1,000, times their own weight in water (measured using distilled water, pH 7.5, 25, 760 mm Hg. absorption within about 30 seconds). However, the absorption or swelling capacity and absorption or swelling time typically varies with each specific superabsorbent polymer.

One class of superabsorbent polymers include combinations of a starch and organic monomers, oligomers, polymers, co-polymers or ter-polymers. They may be manufactured in a variety of ways, for example, the methods described in U.S. Pat. Nos. 4,375,535 and 4,497,930, and can be, for example, the product of grafting corn starch (amylopectin) with acrylonitrile (an acrylic monomer or oligomer). A second class of superabsorbent polymers includes combinations of acrylamide and acrylate polymers, co-polymers and ter-polymers.

All references cited herein are incorporated by reference in their entirety.

The concentration of the iodine forming material may be selected in the article according the ultimate needs and designs of the manufacturer, and the level of ant-bacterial effect desired. The concentration of the iodine gas in the liquid in the absorbent material is one measure of the desired results, and a further measure of the desired results is referred to in the art as the kill percentage, a measure of the percent of a specific bacteria (e.g., E. coli) in a liquid sample that would be killed in 5 minutes by the level of active ingredient present. An example would be that the presence of about 8 parts per million of gaseous iodine dissolved in the aqueous material in the absorbent material would have a kill percentage over 50%. It would be desired, as noted above, to have higher concentrations of gaseous iodine in the liquid so that kill percentages are at least 60%, at least 70%, at least 80% and even at least higher than 90% for targeted bacteria and other microbes. Depending upon the specific bacteria or microbe selected for the measurement, the liquid may have to be provided with at least 10 parts per million (ppm), at least 15 ppm, at least 20 ppm, or at least 25 ppm by controlling the amount of reagents added, the rate of reaction of the reagents, and other controls aimed at keeping the iodine in solution in the liquid, such as providing thickening agents or other materials that would reduce the volatility of the iodine gas from the solution.

EXAMPLES

The two reactants may be provided as a solid carrier medium or separate particulate materials that separate the two reactants until they are in contact with water (as in a soluble carrier such as polyvinyl alcohol, gelatin, amylase, sugars and the like, in pellet, fiber, dust, particle or block form). At least one of the two reactants may be independently coated with a soluble/dispersible coating and the two ingredients kept in a single water-penetrable layer.

Individually coated particles can be provided in water-soluble containers/coverings by using water-soluble or water-dispersible coating materials that are also organic solvent soluble (alcohol soluble) such as PVA, gels, polyvinylpyrrolidone, silica coatings, poly(ether ketones), poly(ester ketones), and the like are applied to the individual particles (one single reagent) or groups of particles (both or all reagents) and prilled, spray dried, or otherwise dried into separate, agglomerated, or packed coated particles. Polyvinyl alcohol may be coated on particles (even water soluble particles as used in the present technology) by use of particle coating technologies such as particle impacting in a fluidized bed or equivalent equipment such as shown in U.S. Pat. No. 6,037,019 (Kooyer).

A simple format, in considering application to agricultural fields for treatment to prevent nematodes or other ground or water-dwelling pests or for any age or stage of pest animal, would include at least the following formats:

1) Separate particulate with separate reactants may be carried in the same container;
2) particulate and separate reactants may be carried in different containers for subsequent separate or joint application;
3) particulate reactants may be carried in the same pellets in an anhydrous condition;
4) the particulate reactants may be adhered to the same or separate carrier materials such as pellets, abrasive particles or capsules;
5) the reactants may be carried in carrier materials dispersed throughout or partially constituting a separate carrier material;

6) capsules or microcapsules of the reactants in water-soluble or water-dispersible shells may be dispersed over the surface; and
7) a film or films (water-soluble, water-dispersible or water-leachable) may carry one or more of the reactants, with the other reactant in a location that released or carried first reactant will be placed into contact with the second reactant in the presence of water.

Other formats and process may be used as long as the presence of water or alcohol on the carrier system enables the generation of gaseous molecular iodine within the carrier in sufficient concentration to act as a sterilizing agent or pesticide.

The following examples are provided as prophetic descriptions of formats for delivery of technology according to the descriptions of the present invention.

Example 1

Prophetic

Fibers would be extruded in a non-aqueous solvent of polyvinyl alcohol in two separate batches in combination with particulate reactants. One set of fibers would comprise 40% by weight of Copper Sulfate and the other set of fibers would comprise 40% by weight of Potassium Iodide. The two separate fibers would blended as 5% by total weight of fabric material into the fiber filled used in a diaper. The relatively low concentration (5%) of total added fiber would be expected to minimally change the properties expected from the fiber fill, except for the additional antimicrobial function, Upon activation by alcohol and/or water into the fibers, the polyvinyl alcohol would dissolve, the two reactants would dissolve in a single solution, the reactants would react, and the gaseous iodine would be produced.

The composition of the present technology provides a local concentration (in the water) of at least 5 ppm and preferably at least 10 parts per million iodine in water carried by the material (that is actual water and/or alcohol supported by the water absorbent material) when the material has 5% by weight of water and/or alcohol present in the water absorbent. The 5% is with respect to the total weight of water to the water absorbent material. The water and/or alcohol absorbing material preferably comprises water absorbing fibers. When providing alcohol, there is usually about 8% water present because of the difficulty in separating water from alcohol, except by expensive processing. The alcohol itself can provide additional anti-microbial activity, so the combination of alcohol and the molecular iodine is particularly effective in the practice of the present technology.

The composition that reacts with water and/or alcohol to form molecular iodine may comprise at least two salts, one of which at least two salts comprises an iodide salt. The at least two salts may be selected from the groups consisting of a) XY and b) Z I, wherein X is a metal, Y is an anion, and Z is an alkali metal, ammonium or alkaline cation. X is preferably a divalent metal cation. Y is preferably selected from carbonate, sulfate, sulfite, phosphate, phosphate, nitrate and nitrite, and Z is preferably selected from the group consisting of lithium, potassium, calcium, magnesium, sodium and ammonium. The composition that reacts with water to form molecular iodine preferably comprises cupric sulfate and potassium iodide.

The articles and compositions may have the iodine forming composition appropriately located within the article. For example, where the article is a hand-wipe sheet or diaper, it may have more than 70% of total composition in a central 50% of volume of the diaper. There is little need for antimicrobial activity on the portions of the diaper contacting the outer portions of the hips. Similarly, there would be little need for such activity along the waistband of the diaper. It is therefore desirable to concentrate the active materials in the diaper where the water (e.g., urine) is likely to be emitted. The iodine would migrate through the path of the water to all wetted areas.

A method of inhibiting microbial growth in an article provides a composition within the article, the composition comprising at lest two compounds that react in the presence of water to produce molecular iodine, and placing the article against the skin of an animal where an aqueous emission from the animal may occur. The method acts so that upon addition of water in an amount of between 10 and 100% by weight of the composition, a concentration of at least 10 parts per million of iodine is produced in the water in less than 15 minutes. The activity of the materials may be increased with respect to halogen releasing ability and volume by adding further halogen releasing components, especially iodates, chlorates, bromates, periodates, perchlorates and/or perbromates as a further reagent (e.g., as above 0% to 200% by weight of the further halogen-releasing components to KI. Metal, non-metal, alkaline and alkali halogens compounds may be used.

Another improvement would be to include starch materials into the composition or the surface to be treated so that the released iodine would cause the standard reaction for starch testing and a blue coloration would appear on the surface to alert caregivers that activation had occurred.

Example 2

Prophetic

Two porous films of water-soluble or water-dispersible material such as mannitol are extruded, the porosity provided by mechanical punching of the film of leaching of materials from the film, as well understood in the art. The separate films would contain 40% by weight of Copper Sulfate and 40% by weight of Potassium Iodide. The films can be used as adjacent or opposite side containers for the fiber fill (preferably with a separate non-dissolvable film).

Example 3

Individual granules of Copper Sulfate and Potassium Iodide are coated with water-soluble/dispersible coatings, preferably in the 2-8 micron thickness range. The uncoated particles would preferably have a diameter of between 5-50 microns so that they could be carried in fiber fill for a diaper without too ready settling out of the fiber fill. The coated particles are mixed into the fiber fill, either alone or with a tacky material (on the fiber or on the particles, such as a partially dried coating on the particles) to avoid separation. The fiber particle blend would constitute the fiber fill in a diaper.

FIG. 1 shows a view of the inside of an opened diaper product 20 and the distribution of compositions according to the present technology. The diaper product 20 is shown with a longitudinal center-line 100 and a horizontal center-line 110 about which are approximately symmetrically disposed wide panels 30, adhesive tabs 40, a central absorbent sheet 24, a stretchable/flexible outer cover layer 32 that may be continuous with the wide panels 30. A sectioned area 26 exposes longitudinal elastic filaments 54 that form the elasticity of the diaper along with the crinkling pattern 52. There are significant indentations 50 on the sides of the diaper t20 to allow fitting to legs. The central absorbent sheet 24 is shown with four separate areas 22 within which there could be the heaviest concentrations of the iodine forming material, and two panels 34 that are towards a more rearward placement on a user where lower concentrations of iodine forming material could be located. Areas outside the central absorbing sheet 24 may have little or no iodine forming materials therein. As noted above, the concentration of the iodine forming materials should be centralized where liquids are more likely to be emitted into the absorbent area and be retained in the absorbent area. The upper region of the diaper and pad 36 and the lower region of the diaper and pad 38 could therefore have less total amount and less concentration of the iodine forming materials then the central area 37. These concentration variations in the vertical direction may also be reflected or substituted with similar regional variations in the horizontal direction of the diaper 20.

The concentration of the iodine forming material may be selected in the article according the ultimate needs and designs of the manufacturer, and the level of ant-bacterial effect desired. The concentration of the iodine gas in the liquid in the absorbent material is one measure of the desired results, and a further measure of the desired results is referred to in the art as the kill percentage, a measure of the percent of a specific bacteria (e.g., *E. coli*) in a liquid sample that would be killed in 5 minutes by the level of active ingredient present. An example would be that the presence of about 8 parts per million of gaseous iodine dissolved in the aqueous material in the absorbent material would have a kill percentage over 50%. It would be desired, as noted above, to have higher concentrations of gaseous iodine in the liquid so that kill percentages are at least 60%, at least 70%, at least 80% and even at least higher than 90% for targeted bacteria and other microbes. Depending upon the specific bacteria or microbe selected for the measurement, the liquid may have to be provided with at least 5 or 10 parts per million (ppm), at least 15 ppm, at least 20 ppm, or at least 25 ppm by controlling the amount of reagents added, the rate of reaction of the reagents, and other controls aimed at keeping the iodine in solution in the liquid, such as providing thickening agents or other materials that would reduce the volatility of the iodine gas from the solution.

Example 3

Prophetic

Particles of KI would be impact coated with smaller particles (1/10 to 1/5 diameter ratio) of polyvinyl alcohol in accordance with the teachings of the processes and equipment shown in U.S. Pat. No. 6,037,019 (Kooyer). These PVA coated particles could then be mixed with particles of cupric sulfate with no concern for any immediate reaction between the salts, even in the presence of ambient moisture. These particles could be carried to the application site for admixture into water to provide iodine or into other carrier material for application to conduit surfaces. It is important to appreciate that both water-borne iodine, alcohol-borne iodine and vapor-borne iodine can be produced in a single environment to address cracks, nooks and crannies in the surfaces to be treated or in the delivery system where intimate contact with water might be difficult.

The activity of the materials may be increased with respect to halogen releasing ability and volume by adding further halogen releasing components, especially iodates, chlorates, bromates, periodates, perchlorates and/or perbromates as a further reagent (e.g., as above 0% to 200% by weight of the further halogen-releasing components to KI. Metal, non-metal, alkaline and alkali halogens compounds may be used.

There are additional or alternative constructions that may be provided within the practice of the present technology, which should not be considered as limited to any specific examples or materials provided. Materials may be coated or adsorbed and attached by van der walls interactions to provide protection. Multiple coatings of same or different materials may be provided over the reagents or to create a layered reagent product. The protective, humidity resistant coating can be liquid (mineral oil, low MW polymers or plasticizers). Materials may be coated as single particle or as an agglomerate The technology of this invention need not be limited to only I2 delivery, but to any system in a superabsorbent carrier material or absorbent carrier material to deliver other antimicrobial activity or any other function, such as odor delivery, catalyst delivery, reagent delivery, light emission (as by reaction of fluoroluminescent reagents), and the like. There are examples of blending untreated CuSO4 and KI in superabsorbent polymers SAP (i.e., color change as a function of time) provided above. Images may actually be displayed with the color changes, providing an entertaining visual display.

All references cited herein are incorporated by reference in their entirety.

What is claimed:

1. A process for the stabilization of two reactants that form iodine in the presence of water comprising:
   providing at least two solid reactants in particulate form that when dissolved or dispersed together in water generate iodine;
   providing a coating on at least one of the at least two reactants in particulate form with a layer that is disruptable, dispersible or soluble in water to form a coated reactant; and
   combining the at least two solid reactants into a single milieu including the coated reactant.

2. The method of claim 1 wherein the coating comprises a stand-off coating of stand-off particles having a diameter that is less than 20% of average particle diameters for the at least one of the at least two reactants.

3. The method of claim 2 wherein the stand-off particles form a discontinuous coating on surfaces of the at least one reactant particles.

4. The method of claim 3 wherein the stand-off particles have a diameter that is less than 10% of average particle diameters for the at least one of the at least two reactants.

5. The method of claim 4 wherein the stand-off particles comprise inorganic oxide particles.

6. The method of claim 1 wherein the coating comprises a coating of a water-soluble material.

7. The method of claim 6 wherein the water-soluble material comprises a water-soluble polymer.

8. The method of claim 1 wherein the coating comprising a coating of a water-dispersible material.

9. The method of claim 8 wherein the water-soluble material comprises a water-dispersible polymer.

10. The method of claim 1 wherein the at least two reactants comprise XY and ZI wherein X is a metal, Y is an anion, Z is an alkali metal or alkaline cation and I is Iodide.

11. The method of claim 1 wherein the at least two reactants comprise $Cu^{+2}SO_4^{-2}$ and $K^+I^-$.

12. The method of claim 4 wherein the at least two reactants comprise $Cu^{+2}SO_4^{-2}$ and $K^+I^-$.

13. The method of claim 5 wherein the at least two reactants comprise $Cu^{+2}SO_4^{-2}$ and $K^+I^-$.

14. The method of claim 8 wherein the at least two reactants comprise $Cu^{+2}SO_4^{-2}$ and $K^+I^-$.

15. The method of claim 1 wherein iodine is released to an environment by contacting the milieu with sufficient aqueous material to breach the coating and allow the at least two reactants to react to generate iodine in the aqueous material.

16. The method of claim 5 wherein iodine is released to an environment by contacting the milieu with sufficient aqueous material to breach the coating and allow the at least two reactants to react to generate iodine in at least the aqueous material, the at least two reactants comprise $Cu^{+2}SO_4^{-2}$ and $K^+I^-$ and the milieu comprises the two reactants as particles, stand-off particles and a carrying medium.

17. The method of claim 7 wherein the at least one coated particle is retained in the milieu by bonding of the water-soluble coating with solid material in the milieu.

18. The method of claim 1 wherein the milieu is selected from the group consisting of a) mixtures of particles, b) mixtures of particles with a carrying medium, c) packets of particles, d) fabric containing particles, e) compacted pellets, and f) combinations of a), b), c), d) and e.

19. The method of claim 18 wherein the milieu comprises fabric in a structured form that retains its shape when contacted with the aqueous material.

20. The method of claim 15 wherein the at least two reactants comprise $Cu^{+2}SO_4^{-2}$ and $K^+I^-$ and the milieu comprises the two reactants as particles, stand-off particles and a carrying medium.

21. The method of claim 19 wherein the at least two reagents, including the at least one coated reagent are combined with fabric material prior to establishing a final structured form of the fabric so that the fabric physically retains the at least two reagents in the structured form.

* * * * *